(12) United States Patent
Teng et al.

(10) Patent No.: US 6,518,294 B2
(45) Date of Patent: Feb. 11, 2003

(54) FUSED PYRAZOLYL COMPOUNDS

(75) Inventors: Che-Ming Teng, Taipei (TW); Sheng-Chu Kuo, Taichung (TW); Fang Yu Lee, Tachia Taichung (TW)

(73) Assignee: Yung Shin Pharmaceutical Ind. Co., Taichung (TW)

( * ) Notice: Subject to any disclaimer, the term of this patent is extended or adjusted under 35 U.S.C. 154(b) by 0 days.

(21) Appl. No.: 10/057,079

(22) Filed: Jan. 24, 2002

(65) Prior Publication Data

US 2003/0004355 A1 Jan. 2, 2003

Related U.S. Application Data

(60) Provisional application No. 60/263,782, filed on Jan. 24, 2001.

(51) Int. Cl.[7] ............. A61K 31/4162; C07D 491/056
(52) U.S. Cl. ..................... 514/403; 548/359.5
(58) Field of Search ............. 548/359.5; 514/403

(56) References Cited

U.S. PATENT DOCUMENTS 5,574,168 A  11/1996  Kuo et al. ............. 548/360.5

FOREIGN PATENT DOCUMENTS

| CA | 2249524 | 6/1999 |
| EP | 0 667 345 A1 | 8/1995 |
| EP | 1 166 785 A | 1/2002 |
| WO | WO 98/16223 | 4/1998 |

OTHER PUBLICATIONS

Kuo et al, *Chemical Abstracts*, vol. 137, No. 25156, 2002.*
Lee et al, Chemical Abstracts, vol. 136, No. 14984, 2001.*
Coughlin et al., "Protease–Activated Receptors and Platelet Function" F.K. Schattauer Verlagsgesellschaft mbH (Stuttgart) 82(2) 353–356 1999.
Coughlin et al., "How the Protease Thrombin Talks to Cells" Proc. National Academy Science USA vol. 96, pp. 11023–11027, Sep. 1999 Colloquium Paper.
Jan Galle et al., "Effects of the Soluble Guanylyl Cyclase Activator, YC–1, on Vascular Tone, Cyclic GMP levels and Phosphodiesterase Activity". British Journal of Pharmacology, vol. 127, 1999. pp. 195–203.
Wu et al., "YC–1 inhibited human platelet aggregation through NO–independent activation of soluble guanylate cyclase," British Journal of Pharmacology, 1995, 116, 1973–1978.
Yu et al., "Inhibition of Platelet Function by A 02131–1, a Novel Inhibitor of cGMP–Specific Phosphodiesterase, In Vitro and In Vivo," Blood, 1996, 87, 3758–3767.
Ko et al., "YC–1, a Novel Activator of Platelet Guanylate Cyclase," Blood, 1994, 84, 4226–4233.

* cited by examiner

*Primary Examiner*—Robert W. Ramsuer
(74) *Attorney, Agent, or Firm*—Fish & Richardson P.C.

(57) ABSTRACT

A fused pyrazolyl compound of the following formula:

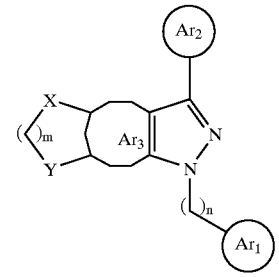

wherein each of $Ar_1$, $Ar_2$, and $Ar_3$, independently, is phenyl, thienyl, pyrrolyl, or furyl, optionally substituted with halo, alkyl, carboxyl, alkoxycarbonyl, thiocarbonyl, aminocarbonyl, hydroxyalkyl, alkoxyalkyl, aminoalkyl, or thioalkyl; each of X and Y, independently, is O, S, or NH; m is 1, 2, or 3; and n is 0, 1, 2, 3, or 4. Also disclosed is a pharmaceutical composition containing a pharmaceutically effective amount of the compound described above.

36 Claims, No Drawings

FUSED PYRAZOLYL COMPOUNDS

CROSS REFERENCE TO RELATED APPLICATION

Pursuant to 35 U.S.C. §119(e), this application claims the benefit of prior U.S. provisional application No. 60/263,782, filed Jan. 24, 2001.

BACKGROUND OF THE INVENTION cGMP, an intracellular secondary messenger, plays an important role in regulating various cellular activities. It is converted from GTP by soluble guanylate cyclase (sGC) and broken down by phosphodiesterases (PDEs). Thus, elevation of the cGMP levels can be achieved by increasing the activity of sGC or reducing the activity of PDEs.

Platelet aggregation contributes to the pathogenesis of various cardiovascular diseases, e.g., atherosclerosis, myocardial infarction, unstable angina pectoris, thrombosis, and hypertension. As low intracellular levels of cGMP cause enhanced platelet aggregation, increasing cGMP levels in platelets provides a way of treating these diseases. Intracellular cGMP levels are also known to influence other physiological functions, e.g., penile erection.

Compounds that boost the intracellular cGMP levels, either by activating sGC or by inhibiting PDEs, have clinical implications for disorders related to low intracellular cGMP levels. Certain pyrazolyl compounds have been found to activate sGC and are potential cardiovascular drugs.

SUMMARY OF THE INVENTION

An aspect of the present invention relates to novel fused pyrazolyl compounds of formula (I):

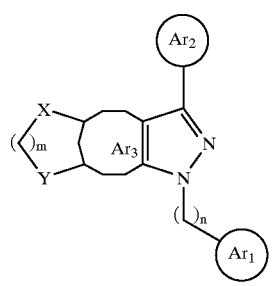

wherein each of $Ar_1$, $Ar_2$, and $Ar_3$, independently, is phenyl, thienyl, pyrrolyl, or furyl, optionally substituted with halo, alkyl, carboxyl, alkoxycarbonyl, thiocarbonyl, aminocarbonyl, hydroxyalkyl, alkoxyalkyl, aminoalkyl, or thioalkyl; each of X and Y, independently, is O, S, or NH; m is 1, 2, or 3; and n is 0, 1, 2, 3, or 4. The term "alkyl," the prefix "alk" (as in alkoxyalkyl), or the suffix "-alkyl" (as in hydroxyalkyl) refers to $C_{1-6}$.

Referring to formula (I), a subset of the compounds of this invention are featured by that X is O, Y is O, and m is 1. In these compounds, $Ar_2$ is preferably phenyl or furyl, or $Ar_3$ is thienyl or phenyl. Another subset of the compounds of this invention are featured by that $Ar_2$ is phenyl or furyl. In these compounds, $Ar_1$ is phenyl, or $Ar_3$ is thienyl or phenyl. Still another subset of the compounds of this invention are featured by that $Ar_3$ is thienyl or phenyl. In these compounds, $Ar_1$ is phenyl and $Ar_2$ is furyl; or $Ar_2$ is phenyl.

Four exemplary compounds of this invention are 1-benzyl-3-(5'-methoxycarbonyl-2'-furyl)-5,6-methylenedioxoindazole, 1-benzyl-3-(5'-hydroxycarbonyl-2'-furyl)-5,6-methylenedioxoindazole, 1-benzyl-3-(5'-methoxymethyl-2'-furyl)-5,6-methylenedioxoindazole, and 1-benzyl-3-(5'-hydroxymethyl-2'-furyl)-5,6-methylenedioxoindazole. The structure of 1-benzyl-3-(5'-hydroxycarbonyl-2'-furyl)-5,6-methylenedioxoindazole is shown below, with the atoms in the aryl rings numbered:

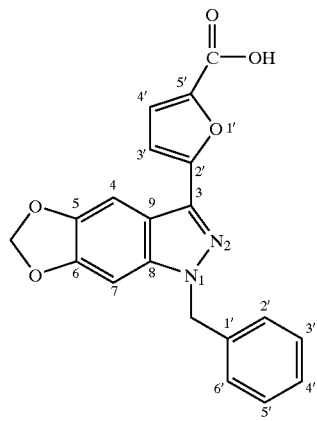

The fused pyrazolyl compounds described above include their salts, if applicable. Such a salt, for example, can be formed between a positively charged substituent, e.g., amino, and an anion. Suitable anions include, but are not limited to, chloride, bromide, iodide. sulfate, nitrate, phosphate, or acetate. Likewise, a negatively charged substituent (e.g., carboxylate) can form a salt with a cation. Suitable cations include, but are not limited to, sodium ion, potassium ion, magnesium ion, calcium ion, and an ammonium cation such as tetramethylammonium ion. Two examples of salts of this invention are the hydrochloride salt of 1-benzyl-3-(5'-aminomethyl-2'-furyl)-5,6-methylenedioxoindazole and the sodium salt of 1-benzyl-3-(5'-carboxyl-2'-furyl)-5,6-methylenedioxo indazole.

Compounds of this invention can activate sGC or inhibiting PDEs.

Thus, another aspect of the present invention relates to a pharmaceutical composition containing an effective amount of a compound of formula (I) and a pharmaceutically acceptable carrier for treating diseases related to low activity of sGC, high activity of PDE, or platelet aggregation.

Details of several embodiments of the invention are set forth in the description below. Other features, objects, and advantages of the invention will be apparent from the description, and also from the claims.

DETAILED DESCRIPTION OF THE INVENTION

A fused pyrazolyl compound of this invention can be synthesized by the following method. React an alkylenedioxoarylacyl chloride with an aryl compound to produce an alkylenedioxoaryl aryl ketone. The ketone is then reacted with a hydrazine to produce a hydrazone, which is subsequently converted to an intermediate in the presence of a first catalyst $Pb(OAc)_4$. Without being purified, the intermediate is further converted to a fused pyrazolyl compound in the presence of a second catalyst $BF_3 \cdot Et_2O$. Desired functional groups, e.g., hydroxy carbonyl or hydroxyalkyl, can be introduced into the fused pyrazolyl compound thus obtained by further modifications.

Shown below is a scheme which depicts the synthesis of four fused pyrazolyl compounds 1, 2, 3, and 4 of this invention:

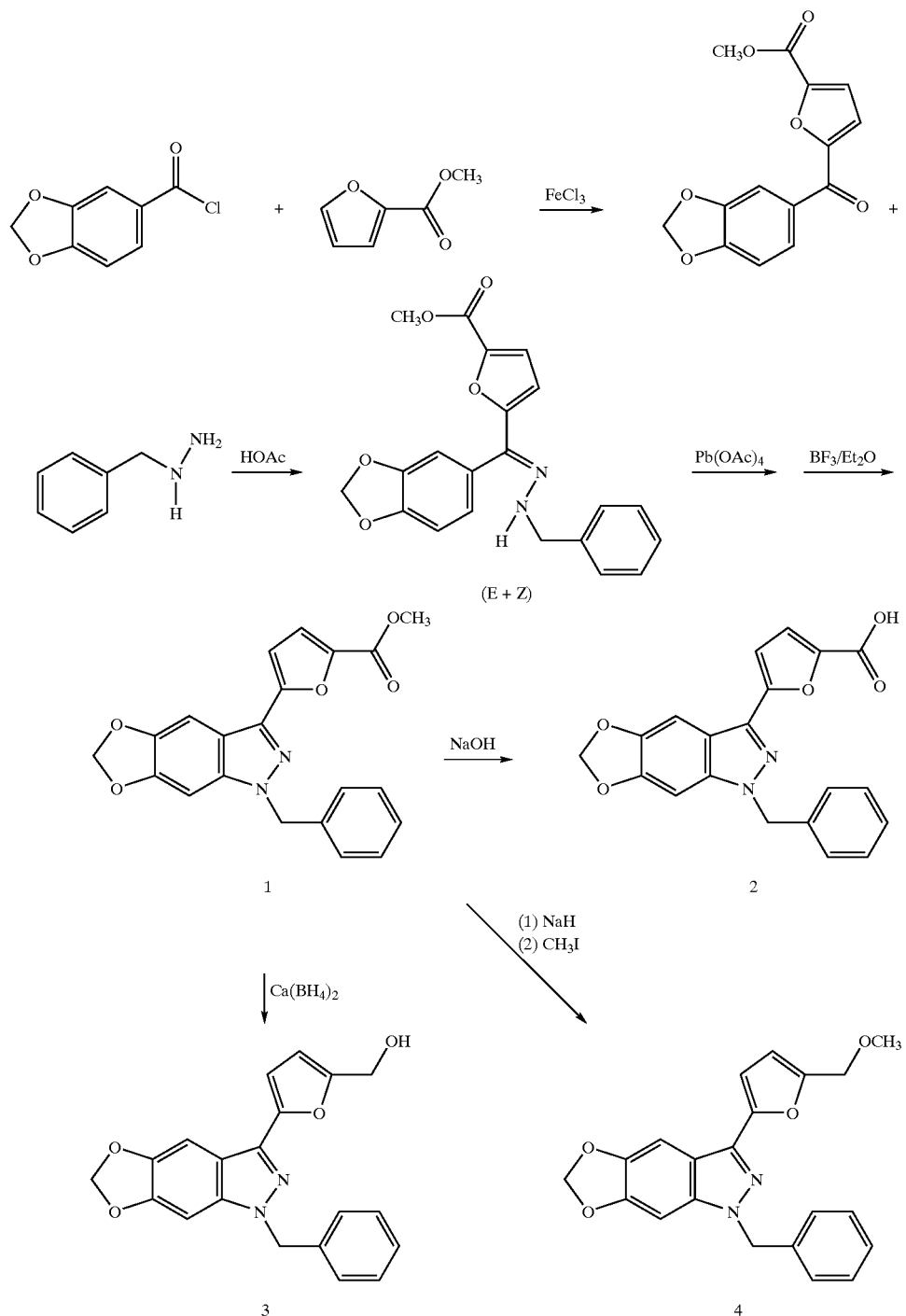

Details of synthesis of compounds 1, 2, 3, and 4 are described in Examples 1, 2, 3, and 4, respectively.

Compounds of this invention can be used to increase the intracellular levels of cGMP by activating sGC or inhibiting PDEs. Thus, another aspect of this invention relates to a pharmaceutical composition which contains an effective amount of at least a fused pyrazolyl compound of formula (I) (or its salt) and a pharmaceutically acceptable carrier for treating diseases associated with low intracellular cGMP levels, e.g., impotence or platelet aggregation-related disorders. "An effective amount" refers to the amount of the compound which is required to confer a therapeutic effect on the treated subject. The interrelationship of dosages for animals and humans (based on milligrams per meter squared of body surface) is described in Freireich et al., Cancer Chemother. Rep., 1966, 50, 219. Body surface area may be approximately determined from height and weight of the patient. See, e.g., Scientific Tables, Geigy Pharmaceuticals, Ardley, N.Y., 1970, 537. Effective doses will also vary, as recognized by those skilled in the art, depending on route of administration, excipient usage, and the possibility of co-usage with other therapeutic treatments including use of other anti-platelet aggregation agents. Examples of the carriers include colloidal silicon dioxide, magnesium stearate, cellulose, sodium lauryl sulfate, and D&C Yellow #10.

The pharmaceutical composition may be administered via a parenteral route, e.g., topically, subcutaneously, intraperitoneally, intramuscularly, and intravenously. Examples of parenteral dosage forms include aqueous solutions of the active compound, in an isotonic saline, 5% glucose, or any other well-known pharmaceutically acceptable carrier. Solubilizing agents, such as cyclodextrins, or other solubilizing agents well known to those familiar with the art, can also be included in the pharmaceutical composition.

A fused pyrazolyl compound of this invention can be formulated into dosage forms for other routes of administration (e.g., orally, mucosally, or percutaneously) utilizing well known methods. The pharmaceutical composition can be formulated, for example, in dosage forms for oral administration in a capsule, a gel seal, or a tablet. Capsules may comprise any well known pharmaceutically acceptable material such as gelatin or cellulose derivatives. Tablets may be formulated in accordance with the conventional procedure by compressing mixtures of the active compounds, a solid carrier, and a lubricant. Examples of solid carriers include starch and sugar bentonite. The compound can also be administered in a form of a hard shell tablet or capsule containing, for example, lactose or mannitol as a binder, a conventional filler, and a tableting agent.

Also within the scope of this invention is the use of a fused pyrazolyl compound of formula (I) for the manufacture of a medicament for the uses described above.

The compounds of this invention can be preliminarily screened for their efficacy in treating the above-described diseases by one or more of the following in vitro assays:

The efficacy of a compound in activating sGC can be evaluated in vitro by the following assay. Washed platelets are suspended in a buffer and disrupted by sonication. The lysate is then centrifuged to obtain a supernatant which is used as the source of sGC. An aliquot of the supernatant and the compound to be tested are added into a buffer containing GTP, a substrate for sGC. The activity of sGC can be determined by the method described in Gerzer et al., J. Pharmacol. Exp. Ther. 1983, 226:180.

The efficacy of a compound in inhibiting PDEs can be evaluated in vitro by the following assay. Washed platelets are suspended in a Tris-HCl buffer and disrupted by sonication. The lysate is centrifuged to obtain a supernatant which contains PDEs. An aliquot of the supernatant is taken to prepare a PDE-containing solution. The compound to be tested and cGMP (a substrate for PDE) are added to the solution. *Ophiophagus hannah* snake venom is subsequently added to remove the phosphate in 5'-GMP (converted from cGMP by PDEs) to form uncharged guanosine. An ion-exchange resin is used to remove the remaining cGMP. The cGMP-free solution is then centrifuged, and an aliquot of the supernatant is taken for quantification of the uncharged guanosine in a liquid scintillation counter. Activity of PDEs is evaluated based on the amount of the uncharged guanosine.

In vitro assays can be used to evaluate the efficacy of a fused pyrazolyl compound of this invention in inhibiting platelet aggregation; which is attributable to low intracellular cGMP levels. For example, the compound is incubated in a platelet suspension containing a platelet aggregation factor, and the degree of aggregation is measured turbidimetrically with a dual-channel lumiaggregometer and converted into a percentage value by the method described in Teng et al.; *Biochem. Biophys Acta.* 1987, 924:375–382.

In vivo screening can be performed by following procedures well known in the art.

Without further elaboration, it is believed that one skilled in the art can, based on the description herein, utilize the present invention to its fullest extent. All publications recited herein are hereby incorporated by reference in their entirety. The following specific examples, which describe synthesis and biological testing of various compounds of the present invention, are therefore, to be construed as merely illustrative, and not limitative of the remainder of the disclosure in any way whatsoever.

EXAMPLE 1

Synthesis of 1-benzyl-3-(5'-methoxycarbonyl-2'-furyl)-5,6-methylenedioxoindazole (Compound 1)

5-Methoxycarbonyl-2-furyl 3',4'-methylenedioxophenyl ketone was first synthesized as follows: Anhydrous ferric chloride (0.42 g, 2.6 mmole) and 3,4-methylenedioxobenzoyl chloride (52.4 g, 0.3 mole) were first dissolved in $CCl_4$ (40 mL). Methyl-2-furoate (25.2 g, 0.20 mmole) was then added dropwise over 10 minutes into the solution. The solution was heated under reflux for 36 hours and then cooled to the room temperature. Water (120 mL) was added into the solution to obtain a mixture. The mixture was stirred for 1 hour and then allowed to sit until it separated into two layers (i.e., a water layer and a $CCl_4$ layer) and a precipitate. The precipitate was collected and dissolved in chloroform. The water layer (on top) was extracted with chloroform. The extract was combined with the solution of the precipitate, dried over anhydrous magnesium sulfate, and filtered. The solvent of the filtrate was removed under reduced pressure to produce a residue. The residue was recrystallized from isopropanol to afford 57.1 g of 5-methoxycarbonyl-2-furyl 3',4'-methylenedioxophenyl ketone in a yield of 56.0%.

mp: 81–82° C.

MS(%), m/z: 274 ($M^+$).

$IR(KBr)\gamma_{max}$: 1716, 1635 $cm^{-1}$ (C=O).

$^1$H-NMR ($CDCl_3$) δ: 3.95 (3H, s, —$OCH_3$); 6.08 (3H, s, —$OCH_2O$—); 7.00 (2H, d, J=10.2 Hz, H-5); 7.27 (2H, S, H-3',4'); 7.56 (1H, d, J=1.7 Hz, C2-H); and 7.79 (2H, dd, J=10.2, 1.7 Hz, H-6).

Elemental analysis C, H (%): calculated 61.32, 3.68; found 61.32, 3.70.

6.6 g (0.024 mole) of 5-methoxycarbonyl-2-furyl 3',4'-methylenedioxophenyl ketone thus obtained was first dissolved in methanol (60 mL). Benzylhydrazine (9.0 g, 0.070 mole) and acetic acid (0.5 mL) were added into the ketone solution. The solution was then heated under reflux until the reaction was completed. After the solution cooled to room temperature, its solvent was removed under vacuum to produce a residue. The residue was extracted with chloroform. The extract was washed sequentially with a dilute HCl solution and water, and dried over anhydrous magnesium sulfate. The dried solution was then filtered, and the solvent of the filtrate was removed to give 5-methoxycarbonylfuryl methylenedioxophenyl ketone benzylhydrazone.

The benzylhydrazone thus obtained was first dissolved in dichloromethane (100 mL). The solution thus obtained was then added dropwise to a Pb(OAc)$_4$ (28.2 g, 0.06 mole) dichloromethane solution (400 mL). The mixture was subsequently heated at 30±2° C. for 30 minutes, followed by the addition of BF$_3$.Et$_2$O (containing 47% of BF$_3$, 122 mL). The mixture was heated under reflux for 30 minutes and then poured into ice water (1000 mL) to terminate the reaction. The organic layer was separated, washed sequentially with water and a 10% sodium carbonate solution, neutralized by water wash, dried over anhydrous magnesium sulfate, filtered, and concentrated under vacuum to an oily crude product. Ethanol was then added to the crude product, and the mixture sit in a refrigerator overnight during which time a precipitate was formed. The precipitate was collected and recrystallized from ethanol to afford 5.7 g of compound 1 in a yield of 63.8%.

mp: 190–192° C.

MS(%), m/z: 376 (M$^+$).

IR(KBr) Y$_{max}$: 1724 cm$^{-1}$ (C=O).

$^1$H-NMR (CDCl$_3$) δ: 3.93 (3H, s, —OCH$_3$); 5.51 (2H, s, =NCH$_2$—); 5.98 (2H, s, —OCH$_2$O—); 6.62 (1H, s, H-7); 6.91 (1H, d, J=3.8 Hz, H-3'); 7.18–7.32 (6H, m, H-4', phenyl); and 7.52 (1H, s, H-4).

Elemental analysis. C, H, N (%): calculated: 67.02, 4.29, 7.44; found: 67.12, 4.31, 7.47.

EXAMPLE 2

Synthesis of 1-benzyl-3-(5'-hydroxycarbonyl-2'-furyl)-5,6-methylenedioxoindazole (Compound 2)

Compound 1 (120 mg, 0.32 mmole) was dissolved in a mixture of methanol (8 mL) and a sodium hydroxide solution (75 mg in 3 mL water). The solution was then heated under reflux. After cooling, the solvents were removed to obtain a residue. The residue was dissolved in water (1.5 mL) and acidified with a diluted HCl solution to obtain a precipitate. The precipitate was collected, and then recrystallized from acetone to afford 87.5 mg of compound 2 in a yield of 75.5%.

mp: 291–292° C.

MS(%), m/z: 362 (M$^+$)

IR(KBr) Y$_{max}$: 3479 cm$^{-1}$ (—OH), 1720 cm$^{-1}$ (C=O)

$^1$H-NMR (DMSO-d$_6$) δ: 5.62 (2H, s, =NCH$_2$—); 6.11 (2H, s, —OCH$_2$—); 7.09 (1H, d, J=3.6, H-3'); 7.20–7.36 (7H, m, H-7,4', phenyl); and 7.43 (1H, s, H-4).

Elemental analysis, C, H, N (%): calculated 66.30, 3.89, 7.73; found 66.35, 3.92, 7.78.

EXAMPLE 3

Synthesis of 1-benzyl-3-(5'-hydroxymethyl-2'-furyl)-5,6-methylenedioxoindazole (Compound 3)

A calcium borohydride solution was first prepared by stirring anhydrous calcium chloride (88.8 mg, 0.8 mmole) with sodium borohydride (60 mg, 1.6 mmole) in anhydrous THF (20 mL) for 4 hrs. A 30 mL THF solution containing 101 mg compound 1 (0.27 mmole) was then added dropwise to the calcium borohydride solution at 30±2° C. The mixture was heated under reflux for 6 hours, cooled, and quenched with ice. The solvent was then removed to obtain a solid product, which was subsequently dissolved in 50 mL dichloromethane. Petroleum ether was then added into the dichloromethane solution to obtain a precipitate. The precipitate was collected and purified by column chromatography (silica gel-benzene) to afford 84.5 mg of compound 3 in a yield of 90%.

mp: 122–123° C.

MS(%), m/z: 348 (M$^+$).

IR(KBr) γ$_{max}$: 3387 cm$^{-1}$ (—OH).

$^1$H-NMR (CDCl$_3$) δ: 2.05 (1H, br, —OH); 4.71 (2H, s, —CH$_2$O—); 5.53 (2H, s, =NCH$_2$—); 5.99 (2H, s, —OCH$_2$O—); 6.43 (1H, d, J=3.3 Hz, H-4'); 6.61 (1H, s, H-7); 6.76 (1H, d, J=3.3 Hz, H-3'); and 7.20–7.31 (6H, m, H-4, phenyl).

Elemental analysis C, H, N (%): calculated: 68.96, 4.63, 8.04; found: 68.92, 4.61, 8.01.

EXAMPLE 4

Synthesis of 1-benzyl-3-(5'-methoxymethyl-2'-furyl)-5,6-methylenedioxoindazole (Compound 4)

0.23 g compound 1 (0.66 mmol) was dissolved in 5 mL THF. To the solution was added 0.8 g NaH (3.3 mmol) at 0±2° C. to obtain a mixture which was allowed to react for 0.5 hour at this temperature. 0.1 g methyl iodide (0.66 mmol) was then added to the reaction mixture. The mixture was stirred for another hour before it was quenched with ice water. The mixture thus obtained was extracted with CH$_2$Cl$_2$, and the extract was neutralized by water, washed, and dried over anhydrous magnesium sulfate. The solvent was removed in vacuo to obtain a residue which was purified by column chromatography (silica gel-benzene) to obtain 0.24 g compound 4 in a yield of 80%.

mp: 99–101° C.

MS(%), m/z: 362 (M$^+$).

IR(KBr) γ$_{max}$: 1635 cm$^{-1}$ (C=O). $^1$H-NMR (CDCl$_3$) δ: 3.42 (3H,S, —OCH3); 4.52 (2H,S, —CH$_2$O—); 5.52 (2H,S, =NCH$_2$—); 5.98 (2H, S, —OCH$_2$O—); 6.48 (1H, d, J=3.3 Hz, H-4'); 6.61 (1H, S, H-7); 6.79 (1H, d, J=3.3 Hz, H-3'); 7.15–7.30 (5H, m, H-4, phenyl); and 7.38 (1H, S, H-4).

Elemental analysis C, H, N (%): calculated: 68.60, 5.01, 7.73; found: 69.58, 5.03, 7.71.

EXAMPLE 5

Activation of sGC

Washed rabbit platelets were prepared by the method described in Teng et al., *Thromb. Haemost.* 1988, 59:304. They were then suspended in 50 mM pH 7.4 Tris-HCl buffer and subsequently disrupted by sonication. The lysate thus obtained was centrifuged at 39,000×g at 4° C. for 20 minutes, and the supernatant was used as the source of sGC. Two 50 μL aliquots of the supernatant were respectively added to two 150 μL pH 7.4 Tris-HCl (50 mM) buffer solutions, each containing GTP (0.2 mM, containing 1×10$^6$ cpm [α-$^{32}$P]GTP), MgCl$_2$ (5 mM), cGMP (2.5 mM), creatine phosphate (15 mM), and creatine phosphokinase (30 μg). One of the two solutions also contained 100 μM compound 3. After incubation at 30° C. for 10 minutes, conversion of GTP to cGMP by sGC was terminated with HCl (200 μL, 0.5 N). The reaction solutions were then heated to 100° C. for 6 minutes and cooled in an ice bath. Following addition of imidazole (200 μL, 1 mM) to each mixture, GTP and cGMP were separated on neutral alumina as described in White et al., *Anal. Biochem.* 1971, 41:372. Radioactivity ([$^{32}$P]cGTP) was measured in a liquid scintillation counter to determine the amount of GTP. The results show that compound 3 was an effective activator of sGC.

EXAMPLE 6

Inhibition of PDE

Washed human platelets were prepared by the method described in Teng et al., *Biochem. Biophys. Acta.* 1989, 990:315–320. They were then suspended in 50 mM pH 7.4 Tris-HCl buffer (containing 5 mM MgCl$_2$) and subsequently disrupted by sonication at 4° C. The lysate thus obtained was centrifuged at 39,000×g at 4° C. for 20 minutes to obtain a supernatant which contained PDEs. Aliquots of the supernatant were taken to prepare two PDE solutions (in a Tris-HCl buffer), one of which contained 10 μM compound 3. Both solutions were first incubated at 37° C. for 5 minutes, followed by addition of 10 μM cGMP (containing 0.1 μCi [$^3$H]cGMP). After further incubation at 37° C. for 30 minutes, during which cGMP was converted to 5'-GMP by PDEs, both solutions were heated to 100° C. for 1 minute and then cooled to the room temperature. *Ophiophagus hannah* snake venom (0.1 mL, 1 mg/mL) was then added, followed by incubation at 25° C. for 30 minutes to convert 5'-GMP to uncharged guanosine. An ion-exchange resin slurry (1.0 mL; Dowex-1, purchased from Sigma Chemical Co., St. Louis, Mo.) was added to each solution to bind and remove any remaining cGMP. Each cGMP-free solution thus obtained was then centrifuged, and an aliquot (0.5 mL) of the supernatant was taken for quantification of uncharged guanosine in a liquid scintillation counter. The results show that compound 3 was a potent inhibitor of PDEs.

EXAMPLE 7

Inhibition of Platelet Aggregation

EDTA was added to blood collected from the marginal ear vein of a rabbit to reach a final EDTA concentration of 6 mM. The EDTA-containing blood was then centrifuged at 90×g for 10 minutes at the room temperature. The supernatant, a platelet-rich plasma, was further centrifuged at 500×g for 10 minutes. The platelet pellets thus obtained were washed with a solution containing EDTA (2 mM) and serum albumin (3.5 mg/mL), and then centrifuged again at 500×g for 10 minutes. The pellets were then washed with an EDTA-free Tyrode's solution of the following composition (mM): NaCl (136.8), KCl (2.8), NaHCO$_3$ (11.9), MgCl$_2$ (1.1), NaH$_2$PO$_4$ (0.33), CaCl$_2$ (1.0), and glucose (11.2). After centrifugation under the same conditions, the platelet pellets were suspended in the EDTA-free Tyrode's solution described above. The platelet number was counted by a Coulter Counter (Model ZM) and adjusted to 4.5×10$^8$ platelets/mL.

A compound to be tested was added to 4 platelet suspensions, which were then incubated at 37° C. for 3 minutes under a stirring condition (900 rpm). One minute after the stirring, four aggregation inducers, i.e., thrombin, collagen, arachidonic acid (AA), and platelet aggregation factor (PAF), were respectively added into the 4 suspensions, causing the platelets to aggregate. Platelet aggregation in each suspension was measured with a dual-channel lumiaggregometer (Model 1020, Payton, Canada) by the turbidimetric method described in Born et al., *J. Physiol.* 1963, 168:178–195. The percentage values of the platelet aggregation, determined 5 minutes after the addition of each aggregation inducer, were calculated by the method described in Teng et al., *Biochem. Biophys Acta.* 1987, 924:375–382.

Compounds 1, 2, 3, and 4 were tested and all showed inhibitory effect on platelet aggregation induced by different inducers. Among them, compound 3 was the most effective in inhibiting platelet aggregation induced by thrombin, AA, collagen, and PAF.

OTHER EMBODIMENTS

A number of embodiments of the invention have been described. Nevertheless, it will be understood that various modifications may be made without departing from the spirit and scope of the invention. For example, the alkylenedioxo group in 1-benzyl-3-(5'-methoxycarbonyl-2'-furyl)-5,6-methylenedioxoindazole can be attached to the fused phenyl group via one or two lower alkylene groups (i.e., C$_{1-2}$). Accordingly, other embodiments are also within the scope of the following claims.

What is claimed is:

1. A fused pyrazolyl compound of the following formula:

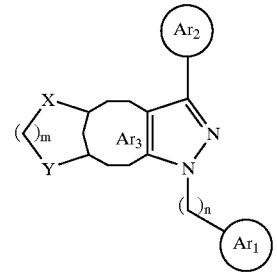

wherein each of Ar$_1$, Ar$_2$, and Ar$_3$, independently, is phenyl, thienyl, pyrrolyl, or furyl, optionally substituted with halo, alkyl, carboxyl, alkoxycarbonyl, thiocarbonyl, aminocarbonyl, hydroxyalkyl, alkoxyalkyl, aminoalkyl, or thioalkyl; each of X and Y, independently, is O, S, or NH; m is 1, 2, or 3; and n is 0, 1, 2, 3, or 4.

2. The fused pyrazolyl compound of claim 1, wherein X is O, Y is O, and m is 1.

3. The fused pyrazolyl compound of claim 2, wherein Ar$_2$ is phenyl or furyl, optionally substituted with halo, alkyl, carboxyl, alkoxycarbonyl, thiocarbonyl, aminocarbonyl, hydroxyalkyl, alkoxyalkyl, aminoalkyl, or thioalkyl.

4. The fused pyrazolyl compound of claim 3, wherein Ar$_1$ is phenyl, optionally substituted with halo, alkyl, carboxyl, alkoxycarbonyl, thiocarbonyl, aminocarbonyl, hydroxyalkyl, alkoxyalkyl, aminoalkyl, or thioalkyl.

5. The fused pyrazolyl compound of claim 3, wherein $Ar_3$ is thienyl or phenyl.

6. The fused pyrazolyl compound of claim 5, wherein $Ar_1$ is phenyl, optionally substituted with halo, alkyl, carboxyl, alkoxycarbonyl, thiocarbonyl, aminocarbonyl, hydroxyalkyl, alkoxyalkyl, aminoalkyl, or thioalkyl.

7. The fused pyrazolyl compound of claim 5, wherein $Ar_3$ is thienyl.

8. The fused pyrazolyl compound of claim 7, wherein $Ar_1$ is phenyl, optionally substituted with halo, alkyl, carboxyl, alkoxycarbonyl, thiocarbonyl, aminocarbonyl, hydroxyalkyl, alkoxyalkyl, aminoalkyl, or thioalkyl.

9. The fused pyrazolyl compound of claim 5, wherein $Ar_3$ is phenyl.

10. The fused pyrazolyl compound of claim 9, wherein $Ar_1$ is phenyl, optionally substituted with halo, alkyl, carboxyl, alkoxycarbonyl, thiocarbonyl, aminocarbonyl, hydroxyalkyl, alkoxyalkyl, aminoalkyl, or thioalkyl.

11. The fused pyrazolyl compound of claim 2, wherein $Ar_3$ is thienyl or phenyl.

12. The fused pyrazolyl compound of claim 11, wherein $Ar_1$ is phenyl, optionally substituted with halo, alkyl, carboxyl, alkoxycarbonyl, thiocarbonyl, aminocarbonyl, hydroxyalkyl, alkoxyalkyl, aminoalkyl, or thioalkyl.

13. The fused pyrazolyl compound of claim 11, wherein $Ar_2$ is furyl, optionally substituted with halo, alkyl, carboxyl, alkoxycarbonyl, thiocarbonyl, aminocarbonyl, hydroxyalkyl, alkoxyalkyl, aminoalkyl, or thioalkyl.

14. The fused pyrazolyl compound of claim 13, wherein $Ar_1$ is phenyl, optionally substituted with halo, alkyl, carboxyl, alkoxycarbonyl, thiocarbonyl, aminocarbonyl, hydroxyalkyl, alkoxyalkyl, aminoalkyl, or thioalkyl.

15. The fused pyrazolyl compound of claim 11, wherein $Ar_2$ is phenyl, optionally substituted with halo, alkyl, carboxyl, alkoxycarbonyl, thiocarbonyl, aminocarbonyl, hydroxyalkyl, alkoxyalkyl, aminoalkyl, or thioalkyl.

16. The fused pyrazolyl compound of claim 15, wherein $Ar_1$ is phenyl, optionally substituted with halo, alkyl, carboxyl, alkoxycarbonyl, thiocarbonyl, aminocarbonyl, hydroxyalkyl, alkoxyalkyl, aminoalkyl, or thioalkyl.

17. The fused pyrazolyl compound of claim 1, wherein $Ar_2$ is phenyl or furyl, optionally substituted with halo, alkyl, carboxyl, alkoxycarbonyl, thiocarbonyl, aminocarbonyl, hydroxyalkyl, alkoxyalkyl, aminoalkyl, or thioalkyl.

18. The fused pyrazolyl compound of claim 17, wherein $Ar_1$ is phenyl, optionally substituted with halo, alkyl, carboxyl, alkoxycarbonyl, thiocarbonyl, aminocarbonyl, hydroxyalkyl, alkoxyalkyl, aminoalkyl, or thioalkyl.

19. The fused pyrazolyl compound of claim 17, wherein $Ar_3$ is thienyl or phenyl.

20. The fused pyrazolyl compound of claim 19, wherein $Ar_1$ is phenyl, optionally substituted with halo, alkyl, carboxyl, alkoxycarbonyl, thiocarbonyl, aminocarbonyl, hydroxyalkyl, alkoxyalkyl, aminoalkyl, or thioalkyl.

21. The fused pyrazolyl compound of claim 19, wherein $Ar_3$ is thienyl.

22. The fused pyrazolyl compound of claim 21, wherein $Ar_1$ is phenyl, optionally substituted with halo, alkyl, carboxyl, alkoxycarbonyl, thiocarbonyl, aminocarbonyl, hydroxyalkyl, alkoxyalkyl, aminoalkyl, or thioalkyl.

23. The fused pyrazolyl compound of claim 19, wherein $Ar_3$ is phenyl.

24. The fused pyrazolyl compound of claim 23, wherein $Ar_1$ is phenyl, optionally substituted with halo, alkyl, carboxyl, alkoxycarbonyl, thiocarbonyl, aminocarbonyl, hydroxyalkyl, alkoxyalkyl, aminoalkyl, or thioalkyl.

25. The fused pyrazolyl compound of claim 1, wherein $Ar_3$ is thienyl or phenyl.

26. The fused pyrazolyl compound of claim 25, wherein $Ar_1$ is phenyl, optionally substituted with halo, alkyl, carboxyl, alkoxycarbonyl, thiocarbonyl, aminocarbonyl, hydroxyalkyl, alkoxyalkyl, aminoalkyl, or thioalkyl.

27. The fused pyrazolyl compound of claim 25, wherein $Ar_2$ is furyl, optionally substituted with halo, alkyl, carboxyl, alkoxycarbonyl, thiocarbonyl, aminocarbonyl, hydroxyalkyl, alkoxyalkyl, aminoalkyl, or thioalkyl.

28. The fused pyrazolyl compound of claim 27, wherein $Ar_1$ is phenyl, optionally substituted with halo, alkyl, carboxyl, alkoxycarbonyl, thiocarbonyl, aminocarbonyl, hydroxyalkyl, alkoxyalkyl, aminoalkyl, or thioalkyl.

29. The fused pyrazolyl compound of claim 25, wherein $Ar_2$ is phenyl, optionally substituted with halo, alkyl, carboxyl, alkoxycarbonyl, thiocarbonyl, aminocarbonyl, hydroxyalkyl, alkoxyalkyl, aminoalkyl, or thioalkyl.

30. The fused pyrazolyl compound of claim 29, wherein $Ar_1$ is phenyl, optionally substituted with halo, alkyl, carboxyl, alkoxycarbonyl, thiocarbonyl, aminocarbonyl, hydroxyalkyl, alkoxyalkyl, aminoalkyl, or thioalkyl.

31. The fused pyrazolyl compound of claim 1, wherein $Ar_1$ is phenyl; $Ar_2$ is furyl, connected to the pyrazolyl ring at its 2-C, and substituted at its 5-C with methoxymethyl, hydroxymethyl, methoxycarbonyl, or hydroxycarbonyl; $Ar_3$ is phenyl, fused at its 1-C and 2-C to the pyrazolyl ring and substituted at each of its 4-C and 5-C with X and Y, respectively; each of X and Y is O, and each of m and n is 1.

32. A pharmaceutical composition, comprising a compound of the following formula:

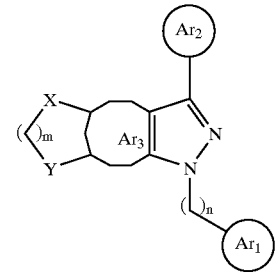

wherein each of $Ar_1$, $Ar_2$, and $Ar_3$, independently, is phenyl, thienyl, pyrrolyl, or furyl, optionally substituted with halo, alkyl, carboxyl, alkoxycarbonyl, thiocarbonyl, aminocarbonyl, hydroxyalkyl, alkoxyalkyl, aminoalkyl, or thioalkyl; each of X and Y, independently, is O, S, or NH; m is 1, 2, or 3; and n is 0, 1, 2, 3, or 4.

33. The pharmaceutical composition of claim 1, wherein X is O, Y is O, and m is 1.

34. The pharmaceutical composition of claim 33, wherein $Ar_2$ is phenyl or furyl.

35. The pharmaceutical composition of claim 33, wherein $Ar_3$ is thienyl or phenyl.
36. The pharmaceutical composition of claim 33, wherein the compound is of the following structure:
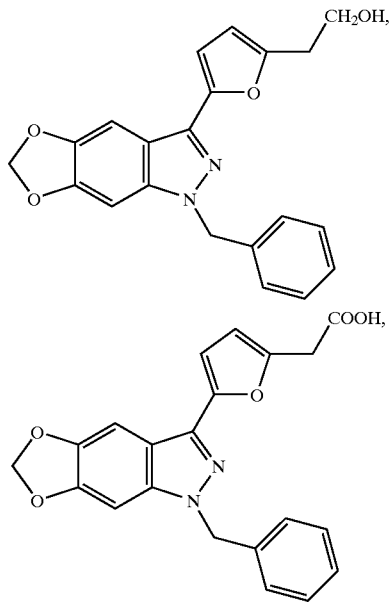
or
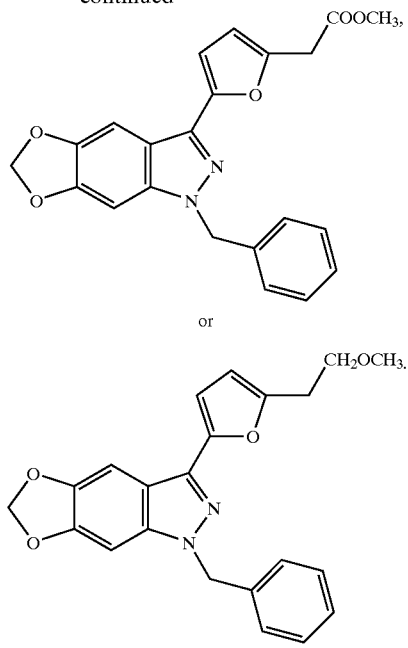
* * * * *